United States Patent
Smith et al.

(10) Patent No.: US 7,329,225 B2
(45) Date of Patent: Feb. 12, 2008

(54) METHODS, DEVICES, SYSTEMS AND COMPUTER PROGRAM PRODUCTS FOR OSCILLATING SHAFTS USING REAL TIME 3D ULTRASOUND

(75) Inventors: Stephen W. Smith, Durham, NC (US); Matthew Fronheiser, Bally, PA (US); Rebecca Booi, Ann Arbor, MI (US); Patrick D. Wolf, Durham, NC (US)

(73) Assignee: Duke University, Durham, NC (US)

( * ) Notice: Subject to any disclaimer, the term of this patent is extended or adjusted under 35 U.S.C. 154(b) by 684 days.

(21) Appl. No.: 10/777,441

(22) Filed: Feb. 12, 2004

(65) Prior Publication Data

US 2004/0230111 A1    Nov. 18, 2004

Related U.S. Application Data

(60) Provisional application No. 60/446,771, filed on Feb. 12, 2003.

(51) Int. Cl.
    *A61B 8/00* (2006.01)
    *A61B 8/14* (2006.01)
    *A61B 19/00* (2006.01)

(52) U.S. Cl. .............. 600/443; 600/461; 128/899; 128/916

(58) Field of Classification Search ........ 600/443–447, 600/454–458, 461, 466–467, 471; 128/899, 128/916
    See application file for complete search history.

(56) References Cited

U.S. PATENT DOCUMENTS

| | | | |
|---|---|---|---|
| 4,694,434 A | 9/1987 | von Ramm et al. ............ 367/7 |
| 5,014,710 A * | 5/1991 | Maslak et al. ............ 600/441 |
| 5,095,910 A * | 3/1992 | Powers ....................... 600/461 |
| 5,158,088 A * | 10/1992 | Nelson et al. ............ 600/461 |
| 5,161,536 A | 11/1992 | Vilmoerson et al. ........ 600/443 |
| 5,329,927 A | 7/1994 | Gardineer et al. .......... 600/439 |
| 5,343,665 A | 9/1994 | Palmersten ................ 52/588.1 |
| 5,413,556 A * | 5/1995 | Whittingham ............... 604/22 |

(Continued)

OTHER PUBLICATIONS

Merdes, Christine L. "Intracardiac Catheter Tracking Using Ultrasonic Volumetric Imaging Fields," Ch. 4, pp. 117-128, Dissertation submitted in partial fulfillment of the requirements for the degree of Doctor of Philosophy, Duke University (2002).

(Continued)

*Primary Examiner*—Francis J. Jaworski
(74) *Attorney, Agent, or Firm*—Myers Bigel Sibley & Sajovec

(57) ABSTRACT

An oscillating shaft is scanned to provide images including the oscillating shaft in vivo in real-time with a real-time three-dimensional (3D) ultrasound scanner. An interventional device can be guided in vivo using an ultrasound scanner and includes a sheath having a bore therethrough from a proximal portion to a spaced-apart distal portion. A shaft has a proximal portion and a spaced-apart distal portion and is configured for insertion into the bore of the sheath. A vibrator is coupled to the proximal portion of the shaft and is configured to cause the distal portion of the shaft to oscillate at a shaft frequency. An isolator is coupled to the proximal portion of the sheath and to the vibrator, wherein the isolator is configured to reduce damping of an oscillation of the shaft by the sheath.

31 Claims, 6 Drawing Sheets

U.S. PATENT DOCUMENTS

| | | | |
|---|---|---|---|
| 5,421,336 | A | 6/1995 | De Benardis ............... 600/461 |
| 5,425,370 | A | 6/1995 | Vilkomerson ............... 600/463 |
| 5,546,807 | A | 8/1996 | Oxaal et al. .................. 73/606 |
| 5,549,112 | A * | 8/1996 | Cockburn et al. .......... 600/461 |
| 5,838,828 | A | 11/1998 | Mizuki et al. ............... 382/236 |
| 5,967,991 | A | 10/1999 | Gardineer et al. .......... 600/461 |
| 5,968,085 | A | 10/1999 | Morris et al. ............... 607/116 |
| 6,066,096 | A * | 5/2000 | Smith et al. ................ 600/439 |
| 6,146,329 | A * | 11/2000 | Hayakawa ................... 600/443 |
| 6,241,675 | B1 | 6/2001 | Smith et al. ................ 600/443 |
| 6,544,178 | B1 | 4/2003 | Grenon et al. .............. 600/443 |
| 6,755,789 | B2 * | 6/2004 | Stringer et al. ............. 600/461 |

OTHER PUBLICATIONS

Ahmad M, Xie TR, McCulloch M, Abreo G, Runge M, Real-time three-dimensional dobutamine stress echocardiography in assessment of ischemia: Comparison with two-dimensional dobutamine stress echocardiography, *J. Amer. Coll. Card.*, 37, pp. 1303-1309, 2001.

Armstrong G, Cardon L, Vilkomerson D, et al. Localization of needle tip with color Doppler during pericardiocentesis: In vitro validation and initial clinical application *J Am Soc Echocardiog* 14 (1), pp. 29-37 Jan. 2001.

Breyer, B. and Cikes, I, Ultrasonically marked catheter—a method for positive echographic guidance of catheters and other minimally invasive medical devices. *Med. and Biol. Eng. and Comput*, 22, pp. 268-271, 1984.

Firek B, Higginbotham M, Russel S, Adams D, Landolfo C, Kisslo J, Initial experience with volume-rendered, real-time three dimensional echocardiography in right ventricular endomyocardial biopsy (abstract), *Eur. Heart J*, 21, pp. 3064, 2000.

McDicken, WN and Andersen T, Ultrasonic stylets for needles and catheters, *Ultras. Med. Biol.*, 10, pp. 499-507, 1984.

Menz V, Vilkomerson D, Ren JF, et al. Echocardiographic transponder-guided catheter ablation feasibility and accuracy, *J Interv Card Electr* 5 (2), pp. 203-209 2001.

Merdes CL and Wolf PD, Locating a catheter transducer in a three-dimensional ultrasound imaging field, *IEEE Trans. Biomed. Eng.* 48, pp. 1444-1452, 2001.

Nicholson NC, McDicken WN A comparison of coupling horns for waveguides used in medical ultrasonics *Ultrasonics* 34 (7), pp. 747-755 Oct. 1996.

Qin JX, Jones M, Shiota T, Greenberg NL, Tsujino H, Firstenberg MS, Gupta PC, Zetts AD, Xu Y, Sun JP, Cardon LA, Odabashian JA, Flamm SD, White RD, Panza JA, Thomas JD, Validation of real-time three-dimensional echocardiography for quantifying left ventricular volumes in the presence of a left ventricular aneurysm: In vitro and in vivo studies, *J. Amer. Coll. Card*, 36, pp. 900-907, 2000.

Ramaswami G, Al-Kutoubi A, Nicolaides AN, et al. Angioplasty of lower limb arterial stenoses under ultrasound guidance: Single-center experience, *J Endovasc Surg* 6 (1), pp. 52-58 Feb. 1999.

Schmidt MA, Ohazama CJ, Agyernan KO, Freidlin RZ, Jones M, Laurienzo JM, Brenneman CL, Arai AE, von Ramm OT, Panza JA, Real-time three-dimensional echocardiography for measurement of left ventricular volumes, *Amer. J. Card.*, 84, pp. 1434-1439, 1999.

Shiota, T, Garcia, MJ, Qin, JX, Drinko, J, Armstrong, G, Greenberg, NL and Thomas JD, Detection of exact location of cardiac catheters using real time 3-dimensional echocardiography, *Jour. Amer. Coll. Card.*, 33, pp. 486A, 1999.

Smith, S. W., Pavy, H.E., and von Ramm, O.T., "High speed ultrasound volumetric imaging system part I: transducer design and beam steering," *IEEE Trans. Ultras. Ferro. and Freq. Control*, UFFC-38, pp. 100-108, 1991.

Tsujino H, Jones M, Shiota T, Qin JX, Greenberg NL, Cardon LA, Morehead AJ, Zetts AD, Travaglini A, Bauer F, Panza JA, Thomas JD, Real-time three-dimensional color Doppler echocardiography for characterizing the spatial velocity distribution and quantifying the peak flow rate in the left ventricular outflow tract, *Ultrasound Med. Biol.*, 27, pp. 69-74, 2001.

Vilkomerson D, Lyons D A system for ultrasonic beacon-guidance of catheters and other minimally-invasive medical devices, *IEEE Trans. Ultras., Ferro. and Freq. Control* 44 (2), pp. 496-504 Mar. 1997.

von Ramm, O.T., Smith, S.W., and Pavy, H.E., "High speed ultrasound volumetric imaging system part II: parallel processing and display" *IEEE Trans. Ultras., Ferro. and Freq. Control*, UFFC-38, pp. 109-115, 1991.

Webster, JG, *Design of Cardiac Pacemakers*, IEEE, New York, NY, pp. 148-149, 1995.

* cited by examiner

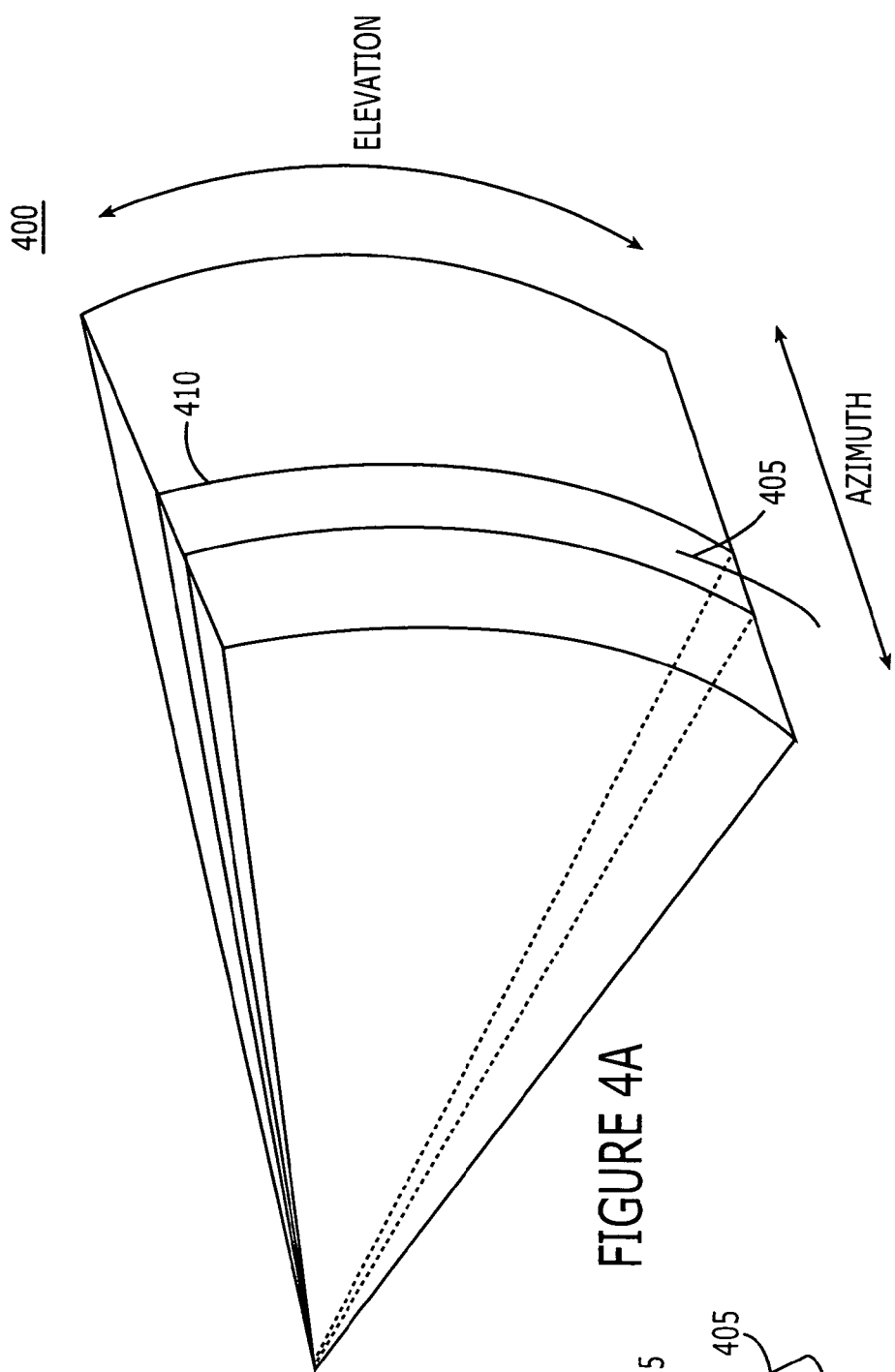
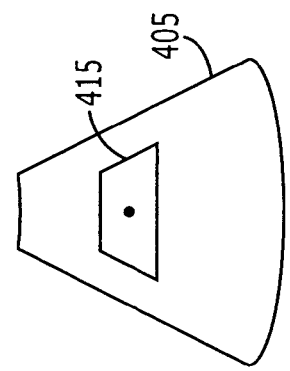
FIGURE 4A
FIGURE 4B

METHODS, DEVICES, SYSTEMS AND COMPUTER PROGRAM PRODUCTS FOR OSCILLATING SHAFTS USING REAL TIME 3D ULTRASOUND

CROSS-REFERENCE TO RELATED PROVISIONAL APPLICATION

This application claims the benefit of Provisional Application Ser. No. 60/446,771, entitled *Guidance of Cardiac Pacemaker Leads Using Real Time 3D Ultrasound*, filed on Feb. 12, 2003, assigned to the assignee of the present invention, the disclosure of which is hereby incorporated herein by reference in its entirety as if set forth fully herein.

STATEMENT OF GOVERNMENT SUPPORT

This invention was made with Government support under grant number HL64962 from the National Institutes of Health. The Government has certain rights to this invention.

FIELD OF THE INVENTION

The invention relates to the field of imaging in general, and more particularly, to ultrasound imaging.

BACKGROUND OF THE INVENTION

Each year in the U.S., more than 100,000 electronic pacemaker systems are implanted to address the effects of cardiac arrhythmias. The pacemaker system can include a pulse generator as well as a lead with tip electrodes that deliver stimulation pulses to the cardiac tissue. To avoid open heart surgical procedures for pacemaker implantation, the lead is threaded through the vessels of the upper venous system, for example, via the subclavian vein to the superior vena cava (SVC), where a tip electrode is coupled to the endocardium within the right ventricular (RV) apex or right atrial (RA) appendage.

The cardiac pacemaker lead is commonly implanted under guidance of single plane fluoroscopy, which may be similar to other minimally invasive cardiac procedures, such as percutaneous catheterization and needle pericardiocentesis. In each of these procedures, the pacemaker lead, the catheter and the needle show high x-ray image contrast. However fluoroscopic guidance may suffer from poor soft tissue contrast, lack of depth information and the risks of ionizing radiation to both patient and health care staff. Accordingly, methods of catheter and needle guidance using ultrasound imaging have been investigated.

It is known that direct ultrasound visualization of a catheter or needle, particularly the tip, is difficult since these are specular reflectors that may appear only intermittently in a conventional ultrasound image. One approach to this problem is to track the catheter by attaching a piezoelectric transducer near the catheter tip which may act as a transmitter or receiver/transponder. For example, the catheter transducer may act as a receiver in the ultrasound field of an imaging transducer. The time of flight from the transmit pulse of the imaging transducer to its reception on the catheter transducer is recorded and used to inject a marker signal in the image at the appropriate depth.

It is also known to use the maximum signal received by the piezoelectric transducer during an ultrasound B-scan to determine the correct image line for the marker signal. For example, an Echomark catheter (Echocath, Princeton, N.J.) has been used with a real time 3D ultrasound scanner (Volumetrics Medical Imaging, Durham N.C.) for cardiac catheter tracking in three dimensions in animal studies. In such studies, spatial cross-correlation was used with stored receive beam profiles to achieve 1% measurement accuracy of the position of the catheter in three dimensions.

It is also known to guide a vibrating needle using a two dimensional ultrasound scanner, as discussed, for example, in *Localization of Needle Tip with Color Doppler During Pericardiocentisis: In Vitro Validation and Initial Clinical Application*, by Armstrong et al., American Society of Echocardiography, 2001, 0894-7317/2001. Other techniques are also discussed, for example, in U.S. Pat. Nos. 5,329,927; 5,421,336; 5,425,370; 5,967,991; and 5,968,085, the disclosures of which are hereby incorporated herein by reference.

SUMMARY

Embodiments according to the invention can provide methods of scanning a shaft in vivo using a three-dimensional (3D) ultrasound scanner. Pursuant to these embodiments, an oscillating shaft is scanned to provide images including the oscillating shaft in vivo in real-time with a real-time three-dimensional (3D) ultrasound scanner.

In some embodiments according to the invention, transmit ultrasound beams are formed from the real-time 3D ultrasound scanner to the oscillating shaft to provide reflected ultrasound energy from the oscillating shaft. Receive ultrasound beams are formed at the real-time 3D ultrasound scanner based on the reflected ultrasound energy from the oscillating shaft. The images are provided based on data generated from the receive ultrasound beams.

In some embodiments according to the invention, the image data is 3D Doppler data, wherein the oscillating shaft is configured to oscillate at an oscillation frequency within an oscillation frequency range. The 3D Doppler data is filtered using a filter having a center frequency about equal to the oscillation frequency and a bandwidth greater than or about equal to the oscillation frequency range. In some embodiments according to the invention, the data includes color Doppler data and echo image data corresponding to a location in a scanned volume. The data is adjusted to attenuate the echo image data and avoid attenuating the color Doppler data at the location in the data.

In some embodiments according to the invention, the data includes 3D Doppler data and echo image data, wherein the images are selected by selecting slice image data from the echo image data based on processing the 3D Doppler data corresponding to the oscillating shaft.

In some embodiments according to the invention, the data includes 3D Doppler data and echo image data, wherein providing the images comprises selecting slice image data from the echo image data that includes a value of the 3D Doppler data corresponding to the oscillating shaft, the value being above a threshold value. In some embodiments according to the invention, the data includes 3D Doppler data and echo image data. A volume rendering of 3D Doppler data is generated which corresponds to the oscillating shaft in real-time.

In some embodiments according to the invention, the slice image data is a first slice image data. A tip of the shaft is tracked in real-time by selecting second slice image data from the echo image data to provide second slice image data responsive to determining that the second slice image data includes a value of the 3D Doppler data corresponding to the oscillating tip of the shaft that is above a threshold value.

In some embodiments according to the invention, the data includes 3D Doppler data and echo image data. A region of interest is defined in the echo image data within which the 3D Doppler data corresponding to the oscillating shaft is generated and outside which 3D Doppler data is not generated. In some embodiments according to the invention, the region of interest is a present region of interest. the present region of interest is changed to a new region of interest in the echo image data based on the present region of interest and an estimate of a new location of a tip of the oscillating shaft.

In some embodiments according to the invention, the data includes 3D Doppler data. A vibrator is activated to cause oscillation of the shaft and enable an audible alarm and the processing of the echo image data to provide 3D Doppler data responsive to a single user input to the real-time 3D ultrasound scanner, wherein the audible alarm is activated responsive to determining that at least a portion of the 3D Doppler data corresponds to the reflected ultrasound energy from the oscillating shaft. In some embodiments according to the invention, the data is 3D Doppler data. An audible alarm is activated responsive to determining that at least a portion of the 3D Doppler data corresponds to the reflected ultrasound energy from the oscillating shaft.

In some embodiments according to the invention, an apparatus for guiding an interventional device in vivo using an ultrasound scanner includes a sheath having a bore therethrough from a proximal portion to a spaced-apart distal portion. A shaft has a proximal portion and a spaced-apart distal portion and is configured for insertion into the bore of the sheath. A vibrator is coupled to the proximal portion of the shaft and is configured to cause the distal portion of the shaft to oscillate at a shaft frequency. An isolator is coupled to the proximal portion of the sheath and to the vibrator, wherein the isolator is configured to reduce damping of an oscillation of the shaft by the sheath.

Related other means and computer program products are also within the scope of the invention.

BRIEF DESCRIPTION OF THE DRAWINGS

FIG. 4A is a schematic illustration of three-dimensional echo data generated by a real-time three-dimensional ultrasound scanner used to scan a region including an interventional device having an oscillating shaft according to some embodiments of the invention.

FIG. 4B is a schematic representation of B-Mode slice image selected from the three-dimensional echo data in FIG. 4A.

DESCRIPTION OF EMBODIMENTS ACCORDING TO THE INVENTION

The invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As will be appreciated by one of skill in the art, the invention may be embodied as methods or devices. Accordingly, the invention may take the form of a hardware embodiment, a software embodiment or an embodiment combining software and hardware aspects.

The invention is also described using a flowchart illustration. It will be understood that each block of the flowchart illustration, and combinations of blocks, can be implemented by computer program instructions. These program instructions may be provided to a processor(s) within an ultrasound scanner, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Figure 1:
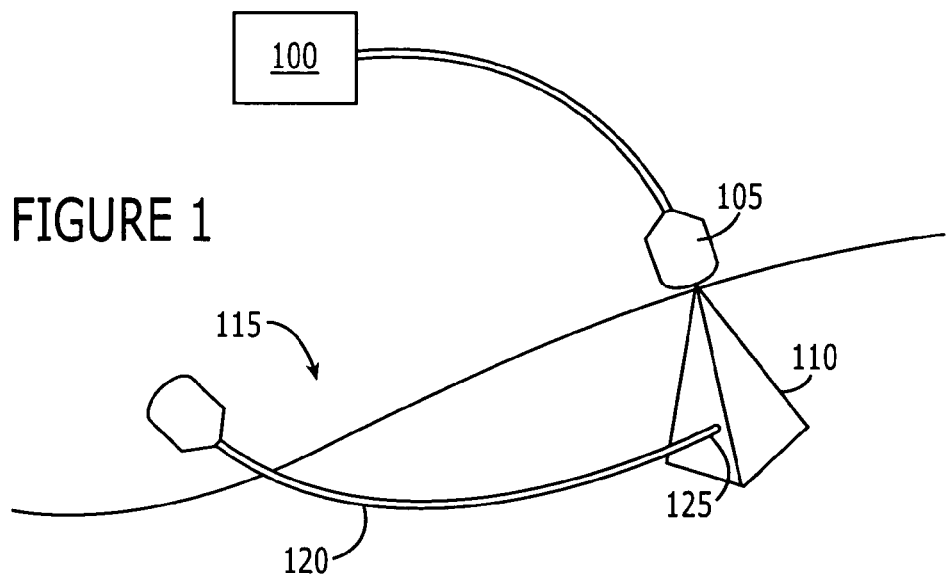
FIG. 1 is a schematic illustration of a real-time three-dimensional ultrasound scanner used to guide an interventional device in vivo having an oscillating shaft according to some embodiments of the invention.

FIG. 1 is a schematic illustration of a real-time three-dimensional (3D) ultrasound scanner 100 used to scan an oscillating shaft of an interventional device 115 to provide real-time images that include the oscillating shaft in vivo. As discussed herein below in greater detail, the interventional device 115 includes, among other things, a shaft 120 with a tip 125 that is configured to oscillate (or vibrate). The interventional device 115 is guided to a portion of an anatomy of interest using images provided by the real-time 3D ultrasound scanner 100 based on echo data 110 which includes at least the tip 125 of the shaft 120. In particular, the real-time 3D ultrasound scanner 100 is configured to generate 3D Doppler data based on the echo data 110 provided by an ultrasound transducer 105. As is well understood by those skilled in the art, the oscillation of the tip 125 can allow the position of the tip 125 to be more discernible in images provided by the real-time 3D ultrasound scanner 100. The tip 125 of the interventional device 115 may be more effectively guided using the real-time 3D ultrasound scanner 100, according to some embodiments of the invention, as the 3D Doppler data produced by the scanner can more clearly indicate the position of the tip 125.

Although embodiments according to the invention are disclosed herein with reference to an oscillating "shaft," it will be understood that the shaft can be any portion of any type of an interventional device which is guided. For example, in some embodiments according to the invention, the shaft can be a pacemaker lead, an ablation electrode, a guidewire (used, for example, during angioplasty), a cryoablation electrode, a needle, or a catheter.

It is known to provide the echo data 110 as three dimensional, or volumetric, ultrasound images using two dimensional ultrasound transducer arrays. For example, U.S. Pat. No. 4,694,434 to von Ramm and Smith discloses a steered phased array acoustic imaging scanner that provides a pyramidal volumetric scan of a region using a two dimensional ultrasound transducer array. It will be understood that the real-time 3D ultrasound scanner 100 can be a scanner disclosed, for example, in U.S. Pat. No. 5,546,807 to Oxaal et al, the entire disclosure of which is incorporated herein by reference. It will be further understood that Oxaal discloses the display of images obtained from a volumetric scanner in which slices of the region scanned can be displayed in real time, where the slices can be, what are sometimes referred to as, B-mode slices, C (Constant) slices, and I (Inclined) slices. It will be understood that although B-mode slices are illustrated in the figures, any of the above type slices can be used in embodiments according to the invention.

Figure 2:
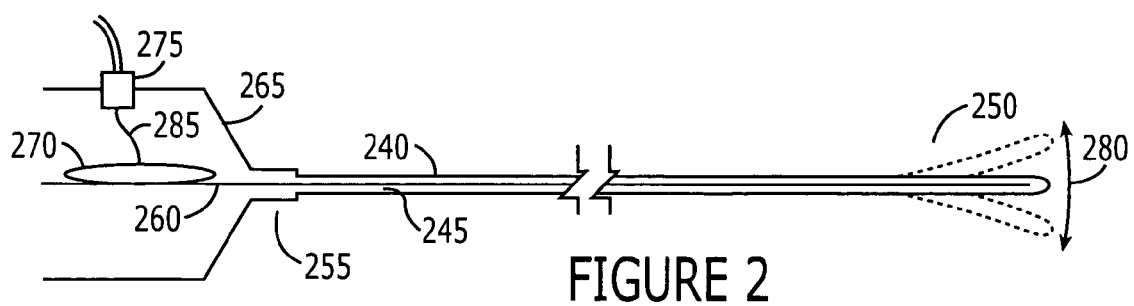
FIG. 2 is a cross-sectional view of an interventional device with an oscillating shaft according to some embodiments of the invention.

FIG. 2 is a cross-sectional view of an interventional device 215 according to some embodiments of the invention. The interventional device 215 includes a sheath 240 having a hollow bore 245 therethrough. The sheath 240 can be closed at a distal portion 250 thereof and open at a proximal portion 255 so that the sheath 240 is configured to allow the insertion of a shaft 260 (or stylet) into the bore 245. The shaft 260 can extend into the bore 245 from the proximal portion 255 to the distal portion 250.

An isolator 265 is coupled to the proximal portion 255. A vibrator 270 is coupled to the shaft 260 and to the isolator 265 via an electrical conductor 285. The vibrator 270 oscillates at a frequency responsive to power provided thereto via the electrical conductor 285 through a connector 275 coupled to the isolator 265. The oscillation of the vibrator 270 is coupled to the shaft 260 via mechanical coupling between the two elements. It will be understood that the shaft 260 can be made vibrate under operator control by supplying power thereto.

In operation, the vibrator 270 vibrates in response to the electrical power to cause the shaft 260 to oscillate along its length. In particular, the portion of the shaft 260 located at the distal portion 250 of the sheath 240 oscillates at a shaft oscillation frequency which is depicted by a movement 280 of a tip of the shaft 260. It will be understood by those skilled in the art that the isolator 265 may allow the strain from the weight of the vibrator 270, which might otherwise be placed on the proximal portion 255 of the shaft 260, to be reduced.

Reducing the strain on the proximal portion 255 of the shaft 260 can reduce a dampening effect on the shaft 260 by the proximal portion of the sheath 240. Without the isolator 265, the weight of the vibrator 270 may otherwise cause the shaft 260 to deflect and make contact with an inner wall of the sheath 240 at the proximal portion 255 thereof. Contact between the proximal portion 255 of the shaft 260 and the sheath 240 may cause a dampening effect on the oscillation of the shaft 260 which may alter the expected response at the tip of the shaft 260, thereby resulting, for example, in reduced or erratic movement 280 of the tip of the shaft 260.

It will be understood that although the cross-section of the interventional device 215 shown in FIG. 2 illustrates an isolator 265 having an open end, other configurations according to embodiments of the invention are also possible. For example, in some embodiments according to the invention, the isolator 265 can be an arm coupled to the proximal portion 255 of the sheath 240. In still other embodiments according to the invention, the vibrator 270 may operate independent of a separate electrical power which may reduce the need for the connector 275 and the electrical conductor 285. In such embodiments according to the invention, the vibrator 270 may operate, for example, using battery power or via power supplied wirelessly thereto.

Figure 3:
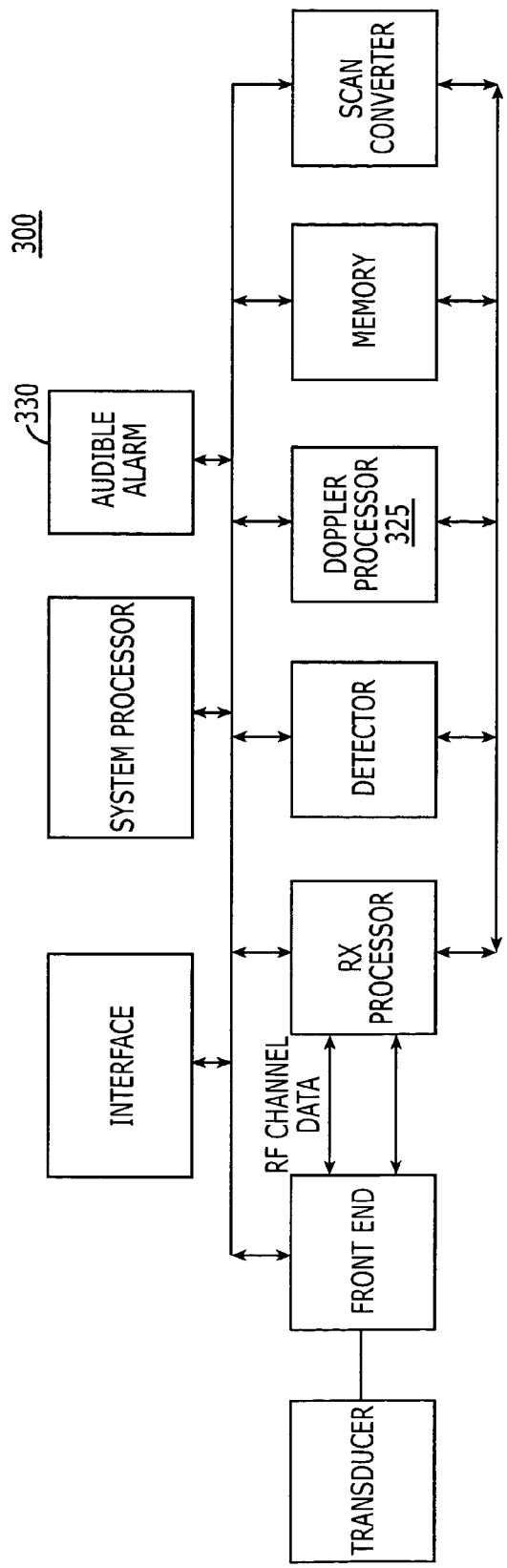
FIG. 3 is a block diagram that illustrates a real-time three-dimensional ultrasound scanner according to some embodiments of the invention.

FIG. 3 is a block diagram that illustrates exemplary functions included in a real-time 3D ultrasound scanner according to some embodiments of the invention. For example, the systems and functions depicted by FIG. 3 are described further in U.S. Pat. No. 6,241,675 to Smith et al., the entire disclosure of which is incorporated herein by reference. According to FIG. 3, a system 300 includes a front end, a RX processor, a detector, and a system processor that may be used to form transmit ultrasound beams from the real-time 3D ultrasound scanner to an oscillating shaft of an interventional device according to some embodiments of the invention. The transmit ultrasound beams are incident upon the oscillating shaft to provide reflected ultrasound energy back to the real-time 3D ultrasound scanner. A portion of the reflected ultrasound energy from the oscillating shaft is received by the real-time 3D ultrasound scanner, which forms receive ultrasound beams based thereon. The receive ultrasound beams can be processed to provide 3D echo data that provides the basis, for example, of image data that can be viewed by a user to guide the interventional device according to some embodiments of the invention.

As shown in FIG. 3, the system 300 also includes a Doppler processor 325. The Doppler processor 325 can be used to process the 3D echo data discussed above to provide 3D Doppler data that is based on the echo data. The 3D echo data can, over time, indicate the movement associated with the oscillating shaft of the interventional device. The movement of the oscillating shaft can make the position of the tip of the shaft be more discernible to a user as the movement of the tip of the shaft typically exceeds other movements which may be indicated by the 3D Doppler data. Moreover, in some embodiments according to the invention, the frequency at which the shaft oscillates can be matched to a filter used by the 3D Doppler processor 325 to filter the 3D echo data. In particular, in some embodiments according to the invention, the center frequency associated with the oscillation of the tip of the shaft of the interventional device may be matched to a center frequency of a bandpass filter used by the Doppler processor 325. The filter may also have an associated bandwidth that is greater than or about equal to a range of frequencies in which the tip of the shaft oscillates. In some embodiments according to the invention, the Doppler processor 325 can adjust the 3D echo data and the 3D Doppler data to attenuate the 3D echo image data and avoid attenuating 3D Doppler data at a location in the data. For example, as is understood by those having skill in the art, 3D Doppler data can be presented as color Doppler data so that different colors on a display represent objects or materials within the anatomy that move at different rates. Accordingly, the echo image data (which is typically represented by grey-scale image data) is attenuated so that the 3D Doppler data (colored or not) is more clearly discernible at the location of interest.

In still further embodiments according to the invention, the Doppler processor 325 can process the data to select slice image data from the echo image data that corresponds to the oscillating shaft of the interventional device. For example, the echo image data can be processed by the Doppler processor 325 to identify which portion of the echo image data includes a Doppler data value that indicates a strong signal, which can be assumed to correspond to the tip of the oscillating shaft. Accordingly, the system 300 can select a slice of image data from the echo image data, where the slice includes the oscillating shaft (i.e. the location within the echo image data that includes the presumed tip of the oscillating shaft). As discussed herein below in great detail, the slices can be selected based on 3D Doppler data values that exceed a threshold or that represent a maximum value.

It will be further understood that in some embodiments according to the invention, the Doppler processor 325 can process the echo image data to produce a three-dimensional rendering of the Doppler data in real-time. The rendering of 3D Doppler data is discussed in greater detail, for example, in U.S. Pat. No. 6,544,178, to Grenon et al. entitled, *Methods and Systems for Volume Rendering Using Ultrasound Data*, the disclosure of which is incorporated herein by reference.

FIG. 4A is a schematic diagram illustrating a volume of 3D echo data 400 scanned by a real-time 3D ultrasound scanner according to some embodiments of the invention. In particular, the 3D echo data 400 includes data corresponding to an oscillating tip 405 of an interventional device according to some embodiments of the invention. As discussed above, the Doppler processor can process the 3D echo data to determine 3D Doppler values for objects within the 3D echo image data 400. Furthermore, in some embodiments according to the invention, the real-time 3D ultrasound scanner can automatically select a B-mode slice of image data 410 that includes the oscillating tip 405 of the shaft. In some embodiments according to the invention, the B-mode slice 405 is determined based on 3D Doppler data indicating movement of an object that is above a threshold value. In some embodiments according to the invention, the B-mode slice 405 is selected by locating a maximum value of the 3D Doppler data in the 3D echo data 400. In still other embodiments according to the invention, the slice 410 is selected based on other indicia associated with fast moving objects, such as the rate of change of the 3D Doppler data within a particular region. For example, the B-mode slice 405 may be selected based on a rate of change of 3D Doppler data such that, for example, a maximum slope indicates the fastest moving portion of the shaft (i.e. the tip 405). It will be further understood that although FIG. 4A shows the shaft and the tip 405 extending in an elevation direction of the 3D echo data 400 within a single B-mode slice 410, the shaft and tip 405 may also extend in the azimuth direction such that the shaft and tip lie in different B-mode slices in the elevation direction.

FIG. 4B is a schematic illustration of a display including the B-mode slice of image data 410 selected from the 3D echo data 400 shown in FIG. 4A. As shown in FIG. 4B, the location of the tip of the shaft 405 can be indicated by 3D Doppler data shown in the slice 405 within a Doppler region of interest 415. It will be understood that the 3D Doppler data shown in FIG. 4B can be 3D color Doppler data.

Figure 5A:
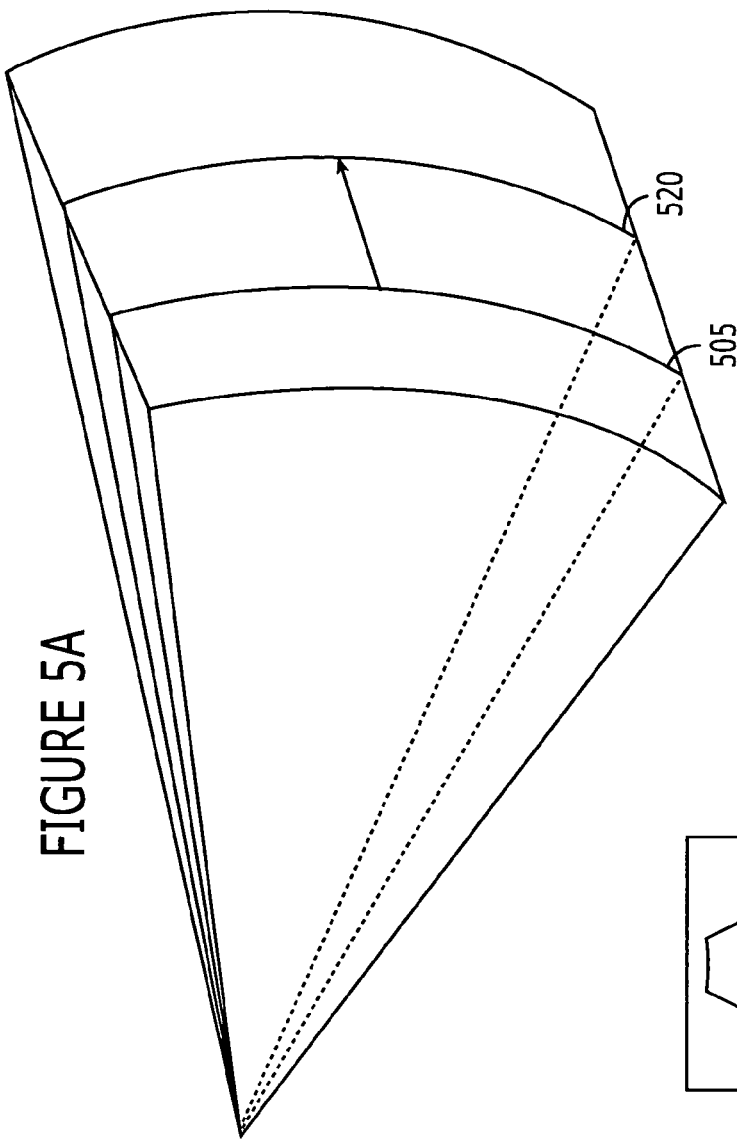
FIG. 5A is a schematic illustration of three-dimensional echo data generated by a real-time three-dimensional ultrasound scanner including first and second B-Mode slice images therein depicting autotracking of an oscillating tip of the shaft according to some embodiments of the invention.
Figure 5C:
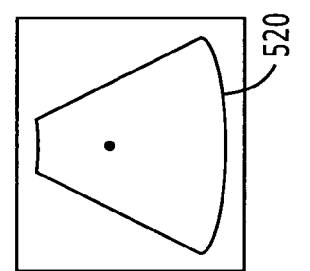
FIGS. 5B and 5C are schematic illustrations of B-Mode slice images corresponding to the slices in FIG. 5A.
Figure 5B:
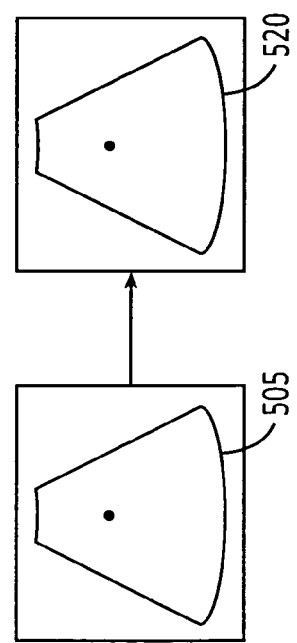

FIG. 5A is a schematic diagram illustrating automatic tracking of an interventional device according to some embodiments of the invention. In particular, a real-time 3D ultrasound scanner is used to provide 3D echo data 500 which includes at least a portion of the interventional device including an oscillating tip thereof. As discussed above in reference to FIGS. 4A-4B, the shaft can be located within the 3D echo data at a position corresponding thereto and can be automatically displayed. Furthermore, as shown in FIG. 5A, the B-mode slice of image data selected for display can be changed as the location of the oscillating tip changes so that the location of the oscillating tip may be automatically tracked by the 3D ultrasound scanner as is guided through the anatomy. In particular, the oscillating tip (not shown) of the shaft is located within the 3D echo data 500 at a first B-mode slice of image data 505. Some time later, the oscillating tip of the shaft is moved to a second location within the 3D echo data 500 included within a second B-mode slice of image data 510. In some embodiments according to the invention, the Doppler processor operates to locate the oscillating tip of the shaft within the 3D echo data 500 within the first slice 505, which can be provided to other portions of the 3D ultrasound scanner so that the first B-mode slice of image data 505 can be provided on a display thereof. As the oscillating tip of the shaft is moved, the Doppler processor locates the oscillating tip of the shaft within the second B-mode slice 510, which is used to update the display of the 3D ultrasound scanner as depicted in FIGS. 5B and 5C. Accordingly, the shaft of the interventional device can be automatically tracked as the shaft is guided through the anatomy.

Figure 6:
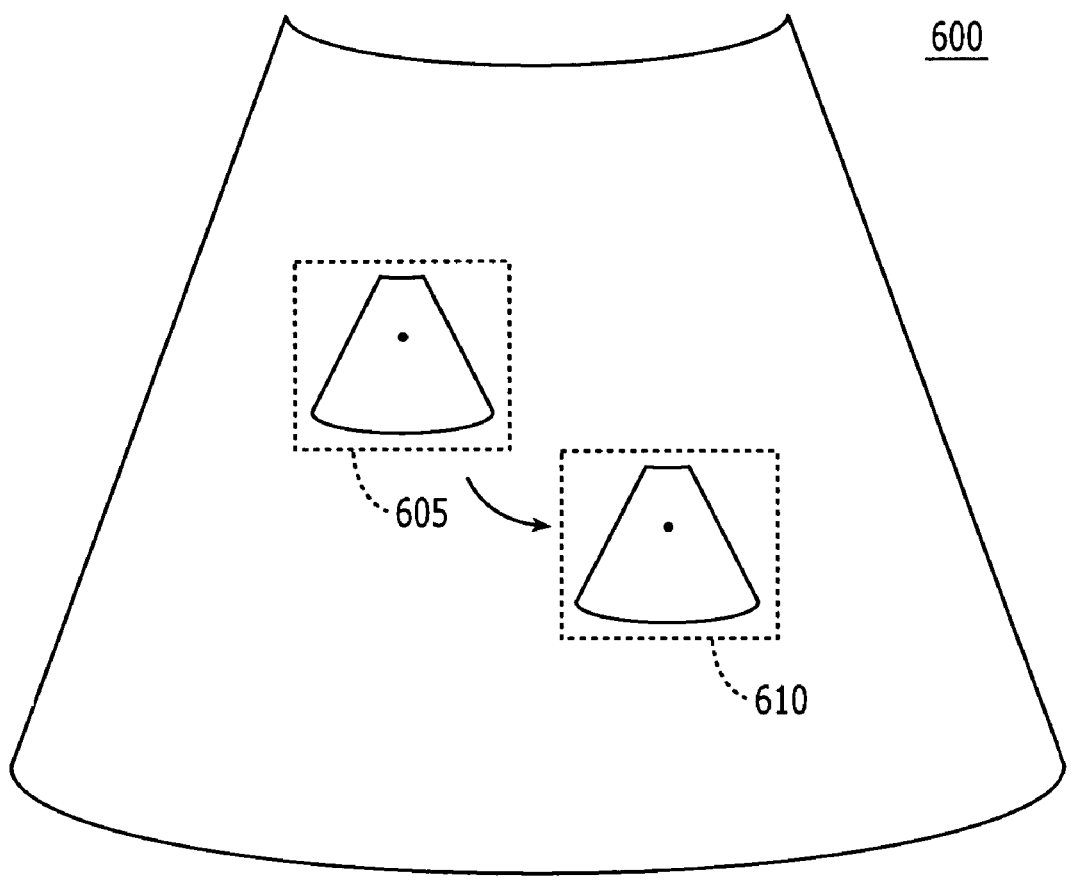
FIG. 6 is a schematic illustration of a B-Mode slice image including changes in a Doppler region of interest therein.

FIG. 6 is a schematic illustration of a display of a B-mode slice of image data 600 by a real-time 3D ultrasound scanner according to some embodiments of the invention. As shown in FIG. 6, a first region of interest 605 can be defined on the display 600 wherein 3D Doppler data is generated by the Doppler processor based on data that falls within the first region of interest 605. It will further be understood that the Doppler processor does not generate 3D Doppler data based on data that is outside the first region of interest 605. As the tip of the shaft of the interventional device moves within the 3D echo data produced by the real-time 3D ultrasound scanner, the tip of the shaft may move on the display 600. Accordingly, the first region of interest may be moved as the tip of the shaft moves on the display 600 so that the Doppler processor may only need to process data corresponding to a location within the 3D echo data that corresponds to the location of the tip of the shaft.

Therefore, as shown in FIG. 6, the first region of interest 605 may be changed to a second region of interest 610 when the location of the tip moves within the display 600. In some embodiments according to the invention, the region of interest is changed from the first region of interest 605 to the second region of interest 610 based on the location of the first region of interest and an estimate of the new location of the tip of the oscillating shaft on the display 600. As understood by those having skill in the art, the estimated motion of the tip on the display 600 can be provided by well-known signal processing techniques. Motion estimation and prediction are discussed, for example, in U.S. Pat. No. 5,838,828, to Mizuki et al., entitled *Method and apparatus for motion estimation in a video signal*, the disclosure of which is incorporated herein by reference.

The system 300 also includes an audible alarm 330 which can operate in conjunction with the Doppler processor and other portions of the system 300 to produce an audible alarm when, for example, the Doppler processor 325 determines that the tip of the shaft is located somewhere within the 3D echo data. Accordingly, an operator may continuously scan the anatomy of interest while coarsely guiding the interventional device toward the anatomy. When the tip of the shaft of the interventional device comes into the proximity of the anatomy of interest such that the Doppler processor 325 detects 3D Doppler data from the oscillating tip (i.e., a strong signal in the frequency band of interest) within the scanned 3D echo image data, the audible alarm is activated so the user may begin guiding the interventional device more finely. In some embodiments according to the invention, the processing of the 3D echo data by the Doppler processor 325 to produce the 3D Doppler data disclosed herein may be operated in conjunction with the audible alarm such that when an operator activates the vibrator (to cause the tip to begin oscillation), the audible alarm 330 is enabled, and the Doppler processor 325 begins processing the 3D echo data to provide the 3D Doppler data used by the system 300.

Figure 7:
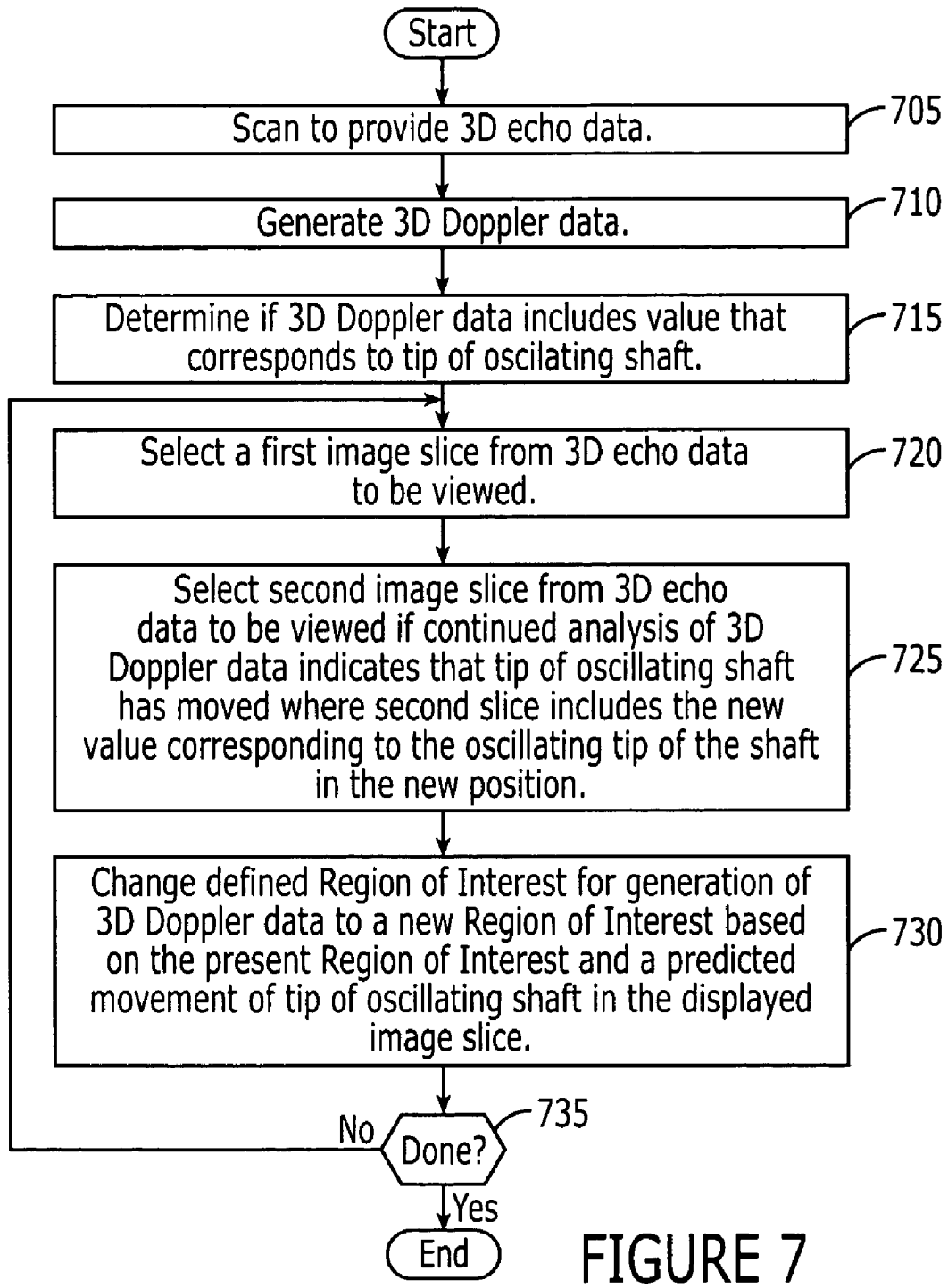
FIG. 7 is a flowchart that illustrates operations of real-time 3D ultrasound scanners according to some embodiments of the invention.

FIG. 7 is a flow chart that illustrates operation of 3D ultrasound scanners according to some embodiments of the invention. In particular, the 3D ultrasound scanner operates to provide 3D echo data (Block 705). The Doppler processor operates on the 3D echo data to provide 3D Doppler data (Block 710). In some embodiments according to the invention, the 3D echo data is filtered according to parameters associated with the oscillation of the interventional device. For example, the tip of the interventional device may oscillate at a frequency that matches the center frequency of the filter applied to the 3D echo data. Furthermore, the Doppler processor may operate to produce 3D Doppler data based on 3D echo data located only within a region of interest so that the amount of echo data processed by the Doppler processor can be reduced to allow an increase in the rate at which the anatomy is scanned. In still further embodiments according to the invention, the Doppler processor may provide 3D Doppler data responsive to user input via the 3D ultrasound scanner.

The Doppler processor determines if the 3D Doppler data includes a value corresponding to the shaft of the interventional device (for example, the tip of the interventional device) (Block 715). If the Doppler processor determines that the 3D echo data includes 3D Doppler values corresponding to the shaft or tip of the interventional device, an audible alarm may be activated. Upon detection that the shaft of the interventional device is located within the 3D echo data, a slice of image data is automatically selected for display (Block 720). As the tip of the shaft moves, the Doppler processor may indicate that another slice of image data should be selected for display as the tip of the shaft has moved within the 3D echo data to outside the presently displayed slice of image data (Block 725). The process in Blocks 720 and 725 is repeated as the tip of the shaft moves throughout the 3D echo data.

As the selected slices of B-mode image data are changed, a region of interest within each of the displayed slices may change based on predictions as to the movement of the tip within the displayed slice changes (Block 730). For example, as the tip of the shaft moves through the 3D echo data, the slices selected for display may change. Furthermore, the region of interest associated with where 3D Doppler data is to be calculated, may alter change. The entire process described from Blocks 705 to 730 can be repeated as the interventional device is guided through the anatomy and additional sets of 3D echo data are generated by the 3D ultrasound scanner (Block 735).

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed is:

1. A method of scanning a shaft in vivo using a three-dimensional (3D) ultrasound scanner, the method comprising:

scanning an oscillating shaft to provide images including the oscillating shaft in vivo in real-time with a real-time three-dimensional (3D) ultrasound scanner, wherein scanning comprises:

forming transmit ultrasound beams from the real-time 3D ultrasound scanner to the oscillating shaft to provide reflected ultrasound energy from the oscillating shaft;

forming receive ultrasound beams at the real-time 3D ultrasound scanner based on the reflected ultrasound energy from the oscillating shaft; and providing the images based on data generated from the receive ultrasound beams;

wherein the data comprises 3D Doppler data and echo image data, and providing the images comprises selecting first slice image data from the echo image data based on processing the 3D Doppler data corresponding to the oscillating shaft, the method further comprising:

tracking a tip of the shaft in real-time by selecting second slice image data from the echo image data to provide second slice image data responsive to determining that the second slice image data includes a value of the 3D Doppler data corresponding to the oscillating tip of the shaft that is above a threshold value.

2. A method according to claim 1, wherein the oscillating shaft is configured to oscillate at an oscillation frequency within an oscillation frequency range, the method further comprising:

filtering the 3D Doppler data using a filter having frequency about equal to the oscillation frequency and a bandwidth greater than or about equal to the oscillation frequency range.

3. A method according claim 1 wherein the data comprises color Doppler data and echo image data corresponding to a location in a scanned volume, the method further comprising:

adjusting the data to attenuate the echo image data and avoid attenuating the color Doppler data at the location in the data.

4. A method according to claim 1, wherein providing the images comprises selecting slice image data from the echo image data that includes a value of the 3D Doppler data corresponding to the oscillating shaft, the value being above a threshold value.

5. A method according to claim 1, the method further comprising:

generating a volume rendering of 3D Doppler data corresponding to the oscillating shaft in real-time.

6. A method according to claim 1, the method further comprising:

defining a region of interest in the echo image data within which the 3 D Doppler data corresponding to the oscillating shaft is generated and outside which 3D Doppler data is not generated.

7. A method according to claim 6 wherein the region of interest comprises a present region of interest, the method further comprising:

changing the present region of interest to a new region of interest in the echo image data based on the present region of interest and an estimate of a new location of a tip of the oscillating shaft.

8. A method according to claim 1, the method further comprising:

activating oscillation of a vibrator to cause oscillation of the shaft and to enable an audible alarm, and processing of the echo image data to provide 3D Doppler data responsive to a single user input to the real-time 3D ultrasound scanner, wherein the audible alarm is activated responsive to determining that at least a portion of the 3D Doppler data corresponds to the reflected ultrasound energy from the oscillating shaft.

9. A method according to claim 1 wherein the data comprises 3D Doppler data, the method further comprising:

activating an audible alarm responsive to determining that at least a portion of the 3D Doppler data corresponds to the reflected ultrasound energy from the oscillating shaft.

10. A method of scanning a shaft in vivo using a three-dimensional (3D) ultrasound scanner, the method comprising:

scanning an oscillating shaft to provide images including the oscillating shaft in vivo in real-time with a real-time three-dimensional (3D) ultrasound scanner, wherein scanning comprises:
  forming transmit ultrasound beams from the real-time 3D ultrasound scanner to the oscillating shaft to provide reflected ultrasound energy from the oscillating shaft;
  forming receive ultrasound beams at the real-time 3D ultrasound scanner based on the reflected ultrasound energy from the oscillating shaft; and
  providing the images based on data generated from the receive ultrasound beams;
wherein the data comprises 3D Doppler data and echo image data, and providing the images comprises selecting first slice image data from the echo image data based on processing the 3D Doppler data corresponding to the oscillating shaft; the method further comprising:

tracking a tip of the shaft in real-time by selecting second slice image data from the echo image data to provide second slice image data responsive to determining that the second slice image data includes a maximum value of the 3D Doppler data corresponding to the oscillating tip of the shaft.

11. An apparatus for guiding an interventional device in vivo using an ultrasound scanner comprising:

a sheath having a bore therethrough from a proximal portion to a spaced-apart distal portion;

a shaft having a proximal portion and spaced-apart distal portion and configured for insertion into the bore of the sheath such that the distal portion of the shaft is fully enclosed by the sheath;

a vibrator coupled to the proximal portion of the shaft and configured to cause the distal portion of the shaft to oscillate at a shaft frequency using a mechanical vibrational coupling; and an isolator coupled to the proximal portion of the sheath and to the vibrator, the isolator configured to reduce damping of an oscillation of the shaft by the sheath and to reduce a strain from a weight of the vibrator on the shaft.

12. An apparatus according to claim 11 wherein the isolator comprises a hollow tube having an open end and an end coupled to the proximal portion of the sheath.

13. An apparatus according to claim 11 further comprising:

an electrical contact for energizing the vibrator coupled to the isolator to reduce contact between the proximal portion of the shaft and the proximal portion of the sheath.

14. A system for scanning a shaft in vivo using a three-dimensional (3D) ultrasound scanner, comprising:

means for scanning an oscillating shaft to provide images including the oscillating shaft in vivo in real-time with a real-time three-dimensional (3D) ultrasound scanner, wherein the means for scanning comprises:
  means for forming transmit ultrasound beams from the real-time 3D ultrasound scanner to the oscillating shaft to provide reflected ultrasound energy from the oscillating shaft;
  means for forming receive ultrasound beams at the real-time 3D ultrasound scanner based on the reflected ultrasound energy from the oscillating shaft; and
  means for providing the images based on data generated from the receive ultrasound beams;
wherein the data comprises 3D Doppler data and echo image data, the means for providing the images comprises means for selecting first slice image data from the echo image data based on processing the 3D Doppler data corresponding to the oscillating shaft. the system further comprising:

means for tracking a tip of the shaft in real-time by selecting second slice image data from the echo image data to provide second slice image data responsive to determining that the second slice image data includes a value of the 3D Doppler data corresponding to the oscillating tip of the shaft that is above a threshold value.

15. A system according to claim 14, wherein the oscillating shaft is configured to oscillate at an oscillation frequency within an oscillation frequency range, the system further comprising:

means for filtering the 3D Doppler data using a filter having a center frequency about equal to the oscillation frequency and a bandwidth greater than or about equal to the oscillation frequency range.

16. A system according claim 14 wherein the data comprises color Doppler data and echo image data corresponding to a location in a scanned volume, the system further comprising:

means for adjusting the data to attenuate the echo image data and avoid attenuating the color Doppler data at the location in the data.

17. A system according to claim 14, wherein the means for providing the images comprises selecting slice image data from the echo image data that includes a value of the 3D Doppler data corresponding to the oscillating shaft, the value being above a threshold value.

18. A system according to claim 14, the system further comprising:

means for generating a volume rendering of 3D Doppler data corresponding to the oscillating shaft in real-time.

19. A system according to claim 14, the system further comprising:

means for defining a region of interest in the echo image data within which the 3D Doppler data corresponding to the oscillating shaft is generated and outside which 3D Doppler data is not generated.

20. A system according to claim 19 wherein the region of interest comprises a present region of interest, the system further comprising:

means for changing the present region of interest to a new region of interest in the echo image data based on the present region of interest and an estimate of a new location of a tip of the oscillating shaft.

21. A system according to claim 14, the system further comprising:

means for activating a vibrator to cause oscillation of the shaft and to enbale an audible alarm, and processing of the echo image data to provide 3D Doppler data responsive to a single user input to the real-time 3D ultrasound scanner, wherein the audible alarm is activated responsive to determining that at least a portion of the 3D Doppler data corresponds to the reflected ultrasound energy from the oscillating shaft.

22. A system according to claim 14, the system further comprising:

means for activating an audible alarm responsive to determining that at least a portion of the 3D Doppler data corresponds to the reflected ultrasound energy from the oscillating shaft.

23. A computer program product for scanning a shaft in vivo using a three-dimensional (3D) ultrasound scanner, comprising:

a computer readable medium having computer readable program code embodied therein, the computer readable program product comprising:

computer readable program code configured to scan an oscillating shaft to provide images including the oscillating shaft in vivo in real-time with a real-time three-dimensional (3D) ultrasound scanner the computer readable program code configured to scan comprises:

computer readable program code configured to form transmit ultrasound beams from the real-time 3D ultrasound scanner to the oscillating shaft to provide reflected ultrasound energy from the oscillating shaft;

computer readable program code configured to form receive ultrasound beams at the real-time 3D ultrasound scanner based on the reflected ultrasound energy from the oscillating shaft; and computer readable program code configured to provide the images based on data generated from the receive ultrasound beams, wherein the data comprises 3D Doppler data and echo image data, and the computer readable program code configured to provide the images comprises computer readable program code configured to select first slice image data from the echo image data based on processing the 3D Doppler data corresponding to the oscillating shaft, the computer program product further comprising:

computer readable program code configured to track a tip of the shaft in real-time by selecting second slice image data from the echo image data to provide second slice image data responsive to determining that the second slice image data includes a value of the 3D Doppler data corresponding to the oscillating tip of the shaft that is above a threshold value.

24. A computer program product according to claim 23, wherein the oscillating shaft is configured to oscillate at an oscillation frequency within an oscillation frequency range, the computer program product further comprising:

computer readable program code configured to filter the 3D Doppler data using a filter having a center frequency about equal to the oscillation frequency and a bandwidth greater than or about equal to the oscillation frequency range.

25. A computer program product according claim 23 wherein the data comprises color Doppler data and echo image data corresponding to a location in a scanned volume, the computer program product further comprising:

computer readable program code configured to adjusting the data to attenuate the echo image data and avoid attenuating the color Doppler data at the location in the data.

26. A computer program product according to claim 23, wherein the computer readable program code configured to provide the images comprises selecting slice image data from the echo image data that includes a value of the 3D Doppler data corresponding to the oscillating shaft, the value being above a threshold value.

27. A computer program product according to claim 23, the computer program product further comprising:

computer readable program code configured to generate a volume rendering of 3D Doppler data corresponding to the oscillating shaft in real-time.

28. A computer program product according to claim 23, the computer program product further comprising:

computer readable program code configured to define a region of interest in the echo image data within which the 3D Doppler data corresponding to the oscillating shaft is generated and outside which 3D Doppler data is not generated.

29. A computer program product according to claim 28 wherein the region of interest comprises a present region of interest, the computer program product further comprising:

computer readable program code configured to change the present region of interest to a new region of interest in the echo image data based on the present region of interest and an estimate of a new location of a tip of the oscillating shaft.

30. A computer program product according to claim 23, the computer program product further comprising:

computer readable program code configured to activate a vibrator to cause oscillation of the shaft and to enable an audible alarm, and processing of the echo image data to provide 3D Doppler data responsive to a single user input to the real-time 3D ultrasound scanner, wherein the audible alarm is activated responsive to determining that at least a portion of the 3D Doppler data corresponds to the reflected ultrasound energy from the oscillating shaft.

31. A computer program product according to claim 23, the computer program product further comprising:

computer readable program code configured to activate an audible alarm responsive to determining that at least a portion of the 3D Doppler data corresponds to the reflected ultrasound energy from the oscillating shaft.

* * * * *

UNITED STATES PATENT AND TRADEMARK OFFICE
CERTIFICATE OF CORRECTION

PATENT NO. : 7,329,225 B2
APPLICATION NO. : 10/777441
DATED : February 12, 2008
INVENTOR(S) : Smith et al.

It is certified that error appears in the above-identified patent and that said Letters Patent is hereby corrected as shown below:

Column 10, Claim 2, Line 42: Please correct "having fre-"
To read -- having a center fre- --

Column 10, Claim 6, Line 65: Please correct "3 D"
To read -- 3D --

Signed and Sealed this

Third Day of June, 2008

JON W. DUDAS
*Director of the United States Patent and Trademark Office*